United States Patent
Seo

(10) Patent No.: US 8,035,761 B2
(45) Date of Patent: Oct. 11, 2011

(54) SHADING DEVICE FOR WELDING HELMET

(76) Inventor: Won Su Seo, Gwang Myeong (KR)

( * ) Notice: Subject to any disclaimer, the term of this patent is extended or adjusted under 35 U.S.C. 154(b) by 1060 days.

(21) Appl. No.: 11/794,268

(22) PCT Filed: Dec. 23, 2005

(86) PCT No.: PCT/KR2005/004489

§ 371 (c)(1), (2), (4) Date: Jun. 26, 2007

(87) PCT Pub. No.: WO2006/071029

PCT Pub. Date: Jul. 6, 2006

(65) Prior Publication Data

US 2008/0092259 A1 Apr. 24, 2008

(30) Foreign Application Priority Data

Dec. 28, 2004 (KR) .................. 10-2004-0113963

(51) Int. Cl.
 *G02F 1/1335* (2006.01)
 *A61F 9/06* (2006.01)
(52) U.S. Cl. .................................. 349/14; 349/16; 2/8
(58) Field of Classification Search .................. None
 See application file for complete search history.

(56) References Cited

U.S. PATENT DOCUMENTS

| 5,533,206 | A  | * | 7/1996  | Petrie et al. .................... 2/8.5 |
| 6,070,264 | A  | * | 6/2000  | Hamilton et al. ................ 2/8.8 |
| 6,973,672 | B2 | * | 12/2005 | Huh .............................. 2/8.1 |
| 7,342,210 | B2 | * | 3/2008  | Fergason ....................... 250/206 |
| 2004/0179149 | A1 | | 9/2004  | Wang-Lee |

* cited by examiner

*Primary Examiner* — Tina M Wong
(74) *Attorney, Agent, or Firm* — Galgano & Associates, PLLC; Thomas M. Galgano; Jessica G. Bower

(57) ABSTRACT

Disclosed is a shading device for a welding helmet in which a circuit portion (the second frame) having a high error rate and the remaining portion can be separated from each other and only the circuit portion separated from the device can be repaired or changed, thereby the maintenance and repair are harmoniously. The shading device for a welding helmet comprising a first frame comprises a first body having a LCD module with contacting portions formed at both sides of a LCD window and a first joint portion formed at one end portion of the first body, a second frame comprising a second body 32 having a power supplying portion and a second joint portion attachable and deattachable to the first joint portion of the first frame at one end portion thereof, a pair of electrodes having one side thereof electrically contacted with the contacting portions respectively, and an electrically conductive means for electrically connecting the power supplying portion with the corresponded electrodes.

10 Claims, 4 Drawing Sheets

[Fig. 1]
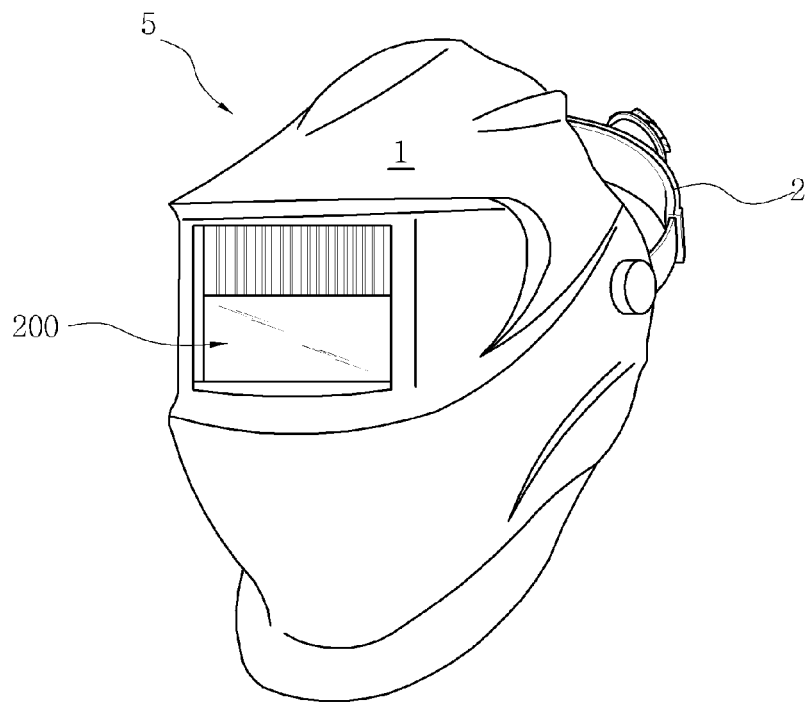
[Fig. 2]
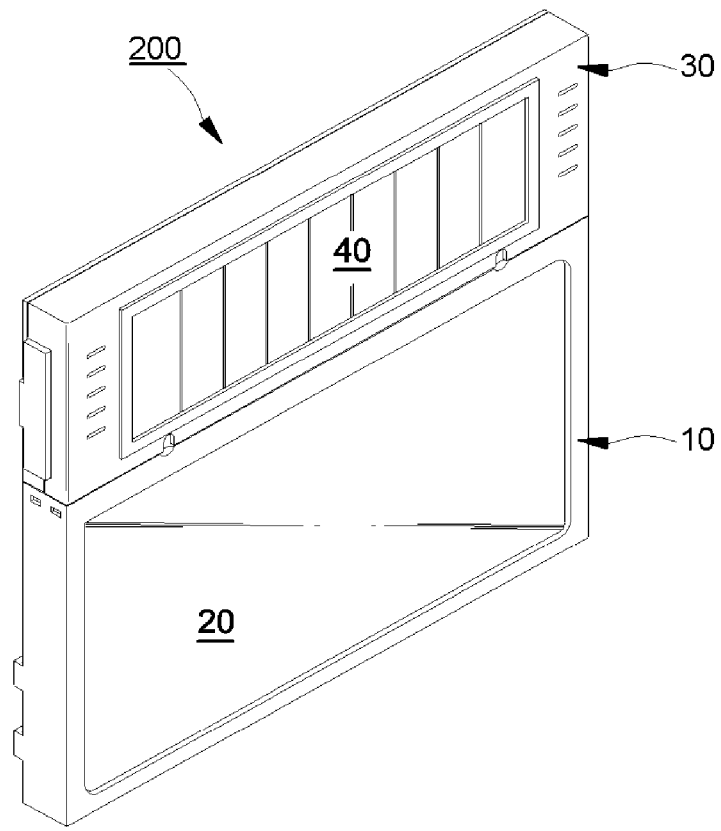

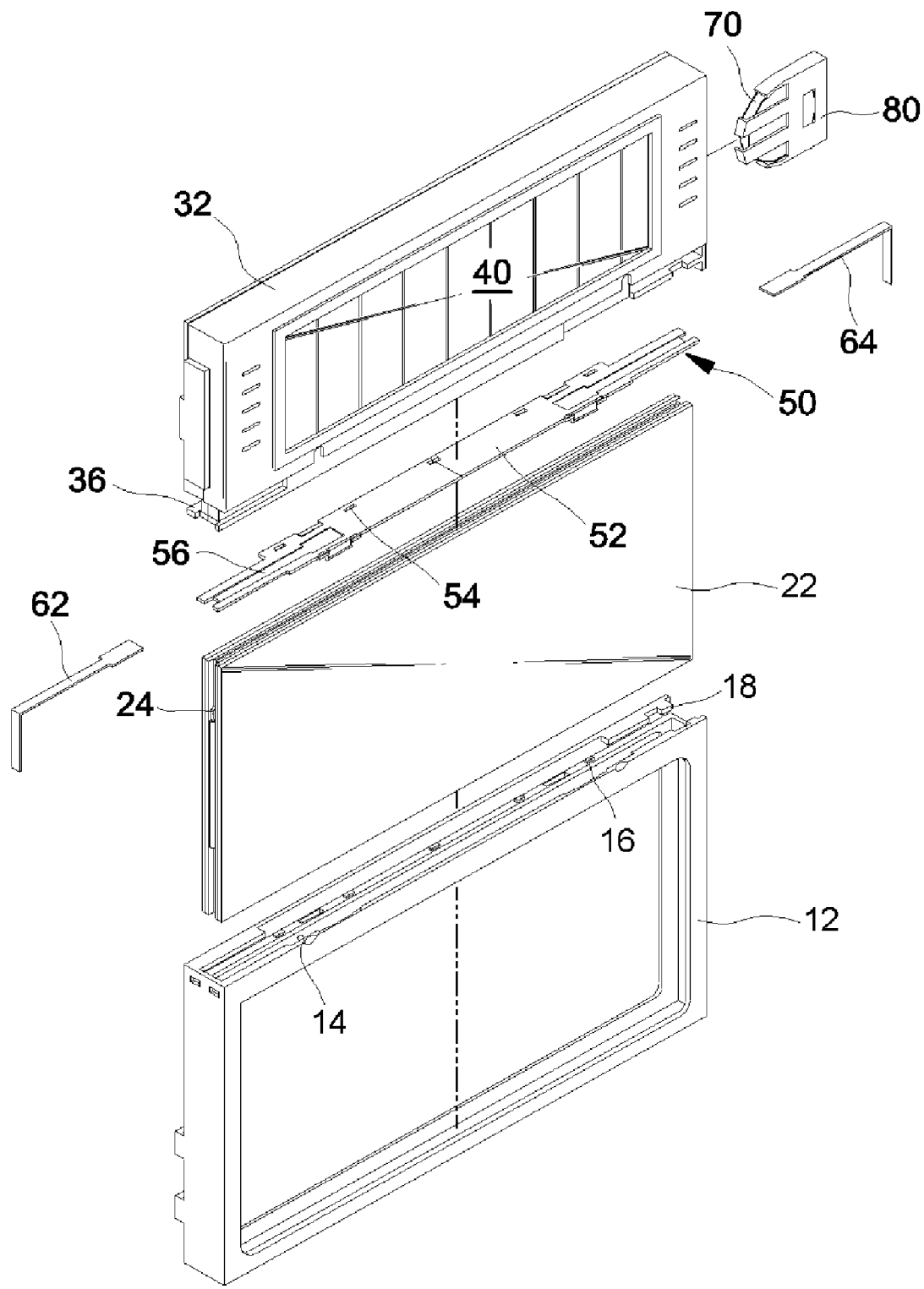
[Fig. 3]

[Fig. 4]
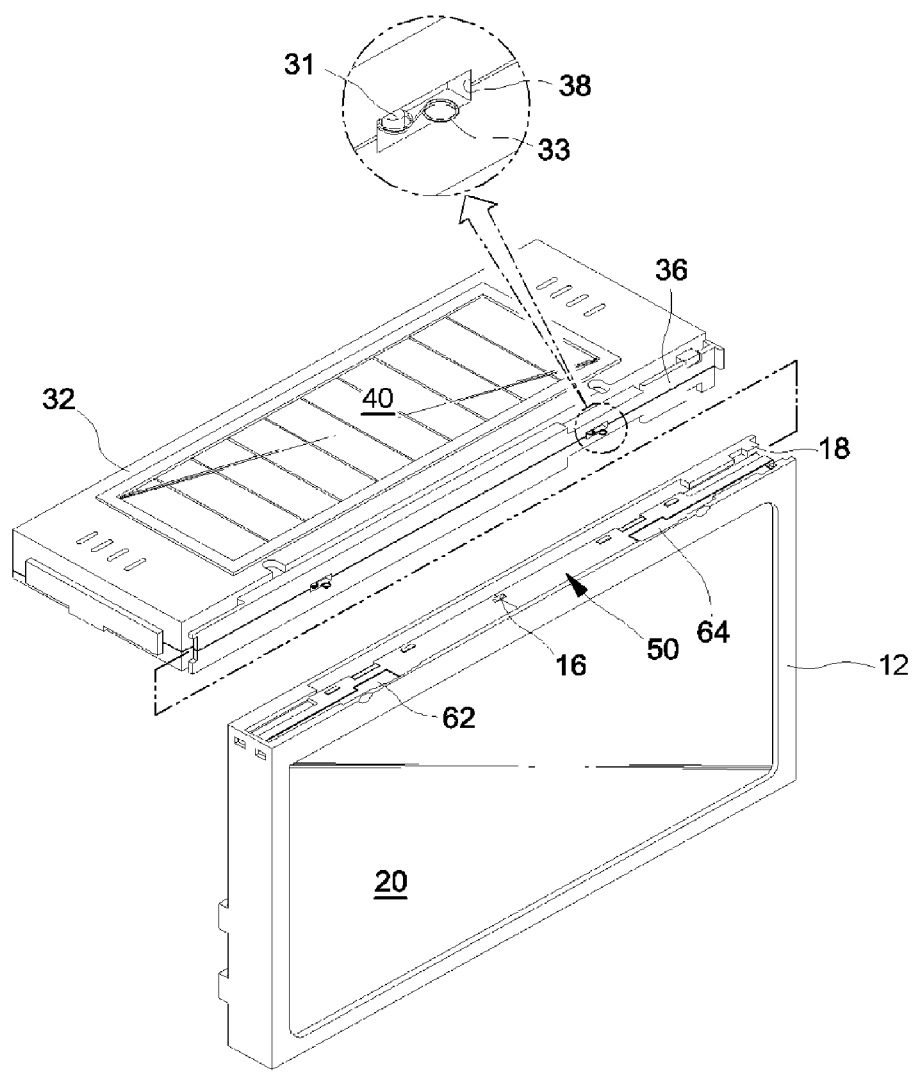
[Fig. 5]
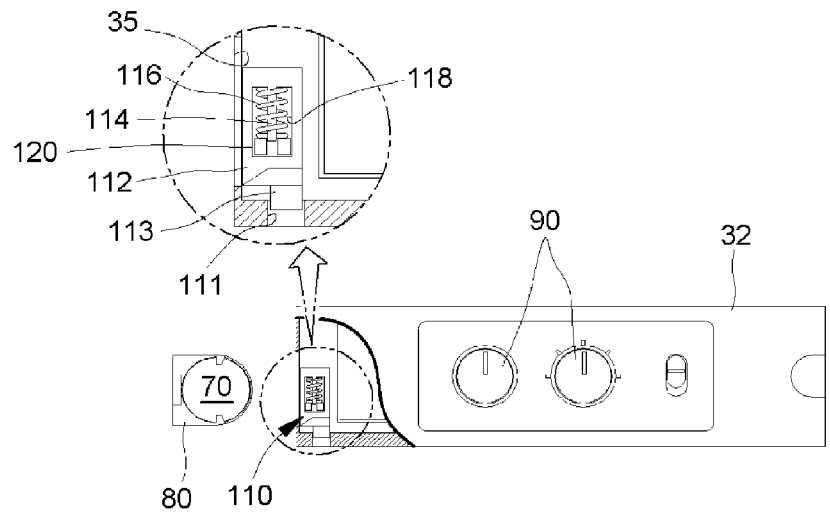

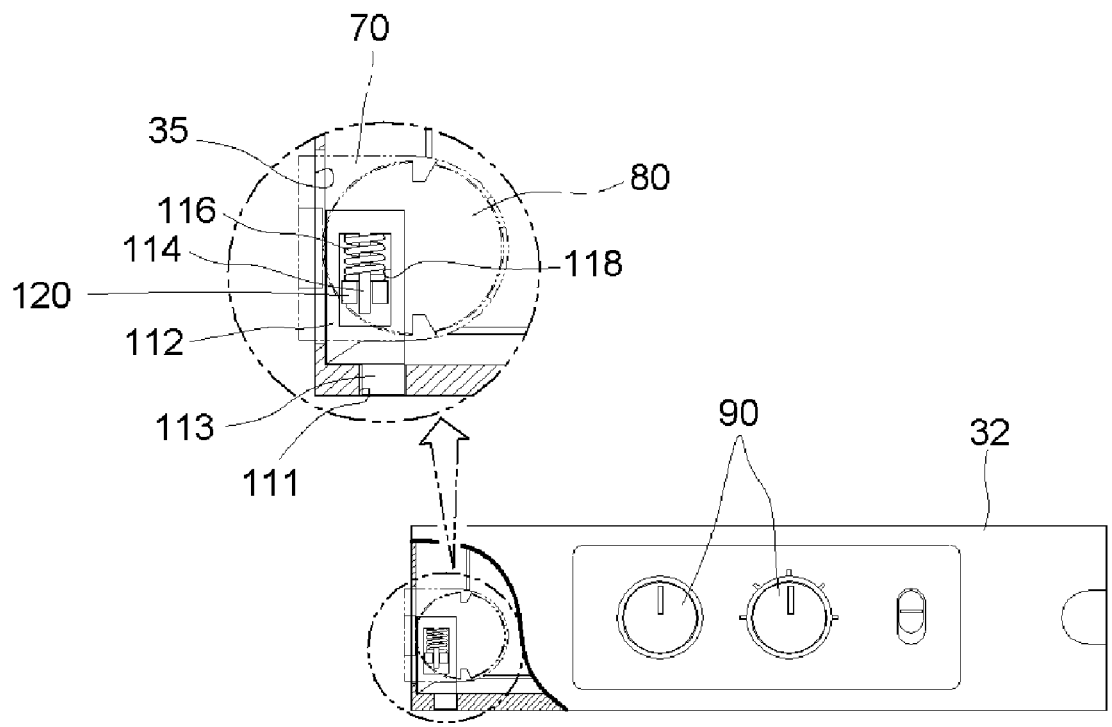
[Fig. 6]

SHADING DEVICE FOR WELDING HELMET

TECHNICAL FIELD

The present invention relates to a shading device for a welding helmet, and more particularly to a shading device for a welding helmet in which a circuit portion having a solar cell module and a shading portion having a LCD module can be separated from each other.

BACKGROUND ART

Generally, the welding helmet serves to protect the eyes and faces of the worker during the welding or cutting process. The welding helmet includes the shading device for preventing the eyes of the worker from the blazing and harmful rays.

U.S. Pat. Nos. 5,533,206 and 6,070,264 disclose welding helmets provided with a shading device, what is called, a cartridge for automatically driving the shade during the welding process. However, there is a problem in that the shading device cannot easily attached or deattached to the welding helmets, so that the maintenance and repair are out of keeping.

In order to solve this problem, Korean Patent publication No. 10-2004-0082771 discloses another welding helmet for easily attaching and deattaching the shading device from the welding helmet.

In the meantime, in the maintenance of the welding helmet having the shading device, it is to be understood that the error rate of the LCD module is very low, but the bulk of the maintenance thereof is due to the error of the circuit portion.

Accordingly, the Korean Patent publication has a merit in that the shading device thereof can be easily attachable and deattachable to easily maintain and repair it. However, in the case of only the circuit portion failure, there is a problem in that the entire shading device is separated from the welding helmet in order to repair it. Especially, since the majority of the shading devices are exported to foreign countries at present, the foreign company must send the whole shading device to the domestic supplier in order to maintain and repair it. Also, there is a problem in that the shading device cannot be used during the maintenance and repair.

Also, where the circuit board cannot be used on account of the break down thereof, the LCD module of good condition should be changed, and in view of the fact that the LCD module has a large majority of the unit cost of the shading device, it causes a serious waste of resources as well as an additional cost unnecessary to the user.

Accordingly, in order to solve the conventional problems, there is an increased desire for the shading device in which it can maintain and repair harmoniously and prevent the unnecessary waste of resources.

DISCLOSURE OF INVENTION

Technical Problem

Accordingly, the present invention has been made to solve the above-mentioned problems occurring in the prior art, and an object of the present invention is to provide a shading device for a welding helmet in which a circuit portion and a shading portion are separated from each other, whereby it can easily change only a bad circuit portion.

Technical Solution

To accomplish the object, the present invention provides a shading device for a welding helmet comprising: a first frame comprising a first body having a LCD module with contacting portions formed at both sides of a LCD window and a first joint portion formed at one end portion of the first body; a second frame comprising a second body having a power supplying portion and a circuit portion and a second joint portion attachable and deattachable to the first joint portion of the first frame at one end portion thereof; a pair of electrodes having one end portion thereof electrically contacted with the contacting portions respectively; and an electrically conductive means for electrically connecting the power supplying portion with the corresponded electrodes.

Preferably, the first joint portion comprises a guide portion formed at a periphery of an upper surface of the first body and a plurality of latching end portions formed at one side portion of the upper surface of the first body and the second joint portion comprises an insertion end portion integrally formed at a lower end portion of the second body and inserted along a guide portion of the first frame for attaching and deattaching.

Preferably, the shading device further comprises an insertion member comprising a third body located at a upper surface of the LCD window, a plurality of insertion holes corresponding to the plurality of latching end portions of the first frame, and electrode grooves formed at both ends of the third body, and the pair of electrodes comprises one end portion electrically contacted with the contacting portions and the other end portion inserted and fixed into the electrode grooves respectively.

Preferably, the first frame further comprises an insertion hole formed at the upper surface of the first body in the lengthwise direction in order to separate the LCD module from the first body.

Preferably, the power supplying portion comprises a solar cell module and a battery having a battery cassette.

Preferably, the shading device for a welding helmet further comprises a locking means for the battery cassette formed at the second body of the second frame for restricting a jointing status between the first and second frame and releasing the restriction thereof, the locking means comprising; a fourth body having a window and a latching end portion formed at a lower end portion thereof; a supporter attached to a upper portion of the second body and traversing the window at right angle; a stopper located at an inside of the window and attached to the second body; a spring for inserting the supporter therein and interposed between the upper portion of the fourth body and the stopper; and an insertion through hole formed at a lower end portion of the second body in order to restrict the latching end portion or release the restriction of the latching end portions by the elasticity of the spring corresponding to the attachment or the deattachment of the battery cassette.

Preferably, the electrically conductive means comprises each opening located at a lower portion of the insertion end portion corresponding to the electrodes, a supporter mounted on an inside of each opening; and each spring comprising one end portion wound on the supporter and the other end portion electrically connected to the corresponded electrodes.

ADVANTAGEOUS EFFECTS

In the shading device for the welding helmet according to the present invention, there are effects in that the circuit portion (a second frame) having a high error rate and the remaining portion can be separated from each other and only the circuit portion separated from the device can be repaired or changed during the failure thereof, thereby the maintenance and repair are harmoniously, as well as it can prevent the interruption of the work on account of the failure of the circuit portion, thereby improving the work efficiency.

Also, there is another effect in that only the circuit portion can be easily changed when it is destroyed or the life span thereof is completed, thereby reducing an additional cost.

BRIEF DESCRIPTION OF THE DRAWINGS

The above as well as the other objects, features and advantages of the present invention will be more apparent from the following detailed description taken in conjunction with the accompanying drawings, in which:

FIG. 1 is a schematic perspective view illustrating a welding helmet provided with a shading device according to the present invention;

FIG. 2 is a schematic perspective view illustrating the shading device for the welding helmet according to the present invention;

FIG. 3 and FIG. 4 are exploded views illustrating assembling conditions of FIG. 2 respectively; and FIG. 5 and FIG. 6 are sectional views illustrating a mounting status of the battery cassette by partially cutting the second frame of FIG. 2.

BEST MODE FOR CARRYING OUT THE INVENTION

A preferred embodiment of the invention will be described in detail below with reference to the accompanying drawings.

FIG. 1 is a schematic perspective view illustrating a welding helmet provided with a shading device according to the present invention, FIG. 2 is a schematic perspective view illustrating the shading device for the welding helmet according to the present invention, and FIG. 3 and FIG. 4 are exploded views illustrating assembling conditions of FIG. 2 respectively.

Referring to FIG. 1 to FIG. 3, the shading device 200 according to the present invention attachable and deattachable to the front portion of the body of the welding helmet 5 includes a first and a second frames 10 and 30 separated from each other. Here, the reference numeral "2" denotes a fixed string member capable of fixing the head of the worker.

The first frame 10 includes a first body 12 of a rectangular frame having a hollow structure in which front and rear surfaces thereof are opened to outside and an insertion hole 14 formed at the upper surface of the first body 12 in the lengthwise direction in order that the LCD module 20 can be inserted into or separated from it and a LCD module 20 inserted into the first body 12. Also, The first frame 10 further includes a plurality of latching end portions 16 attached to the upper surface of the first body 12, for example one side of the upper surface thereof having the insertion hole 14 and a guide portion 18 formed at the periphery of both ends of the upper surface of the first body 12 in order that the second body 32 can be inserted and fixed into the first body 12 by sliding the second body 32 on the guide portion 18.

The LCD module 20 includes a LCD window 22 and two contacting portions 24 for supplying the power to both sides of the LCD window 22.

An insertion member 50 is interposed between the first frame 10 and the second frame 30 in order to connect the first frame 10 and the second frame 30 electrically. The insertion member 50 includes a third body 52 of strip, a plurality of insertion holes 54 corresponding to the plurality of latching end portions 16 formed at the first body 12 respectively, and electrode grooves 56 formed at both ends thereof.

A pair of symmetric electrodes 62 and 64 includes one end portion side inserted and fixed into the electrode groove 56 and the other end portion contacted with the contacting portions 24 formed at both sides of the LCD window 22 respectively.

The second frame 30 has a solar cell module 40 and a battery 70. Here, the battery 70 contained in a battery cassette 80 can be attached and deattached to the second frame 30.

The second frame 30 includes the second body 32 of a rectangular frame having the solar cell module 40 and the battery 70 and an insertion end portion 36 integrally formed at the lower portion of the second body 32 in order to insert it into the guide portion 18, which is formed at the first body 12 of the first frame 10.

Here, electrically conductive means are formed at the lower portion of the second body 32 that is, the lower portion of the insertion end portion 36 so as to electrically connect with the solar cell module 40 and the battery 70. The electrically conductive means includes openings 38 located at the lower portion of the insertion end portion 36 corresponding to the electrodes 62 and 64 and springs 33 as an electrode located at the inside of each opening 38 so as to electrically connect with the solar cell module 40 and the battery 70.

Each spring 33 includes one end portion wound on a supporter 31 mounted on the inside of the opening 38 and the other end portion partially protruded from the opening 38 in order to electrically connect with the corresponded electrodes 62 and 64 during the combining of the first frame 10 and the second frame 30.

In the shading device 200 in accordance with this structure of the present invention, since the second frame 30 is inserted into or separated from the first frame 10 by sliding the insertion end portion 36 along the guide portion 18, only second frame (circuit portion) 30 having a high error rate can be changed, thereby resolving the conventional problem.

FIG. 5 and FIG. 6 are sectional views illustrating a mounting status of the battery cassette by partially cutting the second frame of FIG. 2.

Referring to FIG. 5, the shading device 200 according to the present invention further includes a locking means for the battery cassette in order that the second frame 30 is not separated from the first frame 10 in the combined state thereof.

The locking means for the battery cassette includes a fourth body 112 having a window 118 and a latching end portion 113 formed at the lower end portion thereof, a supporter 114 attached to the upper portion thereof and traversing the window 118 at right angle, a stopper 120 located at the inside of the window 118 and attached to the second body 32, a spring 116 inserting the supporter 114 and interposed between the upper portion of the fourth body 112 and the stopper 120, and an insertion through hole 111 formed at the lower end portion of the second body 32 in order to restrict the latching end portion 113 or release the restriction of the latching end portions 113 by the elasticity of the spring 116 corresponding to the attachment or the deattachment of the battery cassette 80.

The latching end portion 113 is comparatively protruded toward the upper portion in comparison with the other portion of the fourth body 112, so as to contact it with the part of the lower end of the battery cassette 80 during the attachment of the battery cassette 80. Also, since the part of the latching end portion 113 contacted with the battery cassette 80 is slanted, the latching end portion 113 goes down during the attachment of battery cassette 80. On the contrary, the latching end portion 113 goes up by means of the elasticity of the spring 116 during the deattachment of battery cassette 80.

Accordingly, in the case of attaching the battery cassette 80 to the second frame 30, the latching end portion 113 goes down and is hung on the first frame 10, so that the first frame 10 and the second frame 30 are not separated from each other. On the contrary, in the case of deattaching the battery cassette 80 to the second frame 30, the latching end portion 113 goes up again by means of the spring 116 and the latching thereof is released, so that the first frame 10 and the second frame 30 can be separated from each other.

Here, the battery cassette 80 is inserted into or separated from the second frame 32 by means of a battery cassette attachment 35 formed at one end portion of the second frame 32.

As though the two frames are attached and deattached to each other by means of the sliding method in the above embodiments, the present invention is not limited to the sliding method and various attachable/deattachable methods can be contained in the embodiments.

INDUSTRIAL APPLICABILITY

Accordingly, it is to be understood that various attachable/deattachable methods such as a button type (both frames separated from each other by pressing the button), an insertion type, a hanger combination type method (a hanger formed at one frame combined with a hanger recess formed at the other frame) and so on can be included within the scope of the present invention.

While this invention has been described in connection with what are presently considered to be the most practical and preferred embodiments, it is to be understood that the invention is not limited to the disclosed embodiments and the drawings, but, on the contrary, it is intended to cover various modifications and variations within the spirit and scope of the appended claims.

The invention claimed is:

1. A shading device for a welding helmet comprising:
a first frame comprising a first body with an upper end portion and an upper surface having side portions, said first body having an LCD module having an LCD window with two opposite sides and an upper surface and a contacting portion formed at each of said opposite sides of said LCD window and a first joint portion formed at said upper end portion of said first body, and wherein said first frame has a first joint portion comprising a guide portion formed adjacent to said upper surface of said first body and a plurality of latching end portions formed at one of said side portions of said upper surface of said first body;
a second frame comprising a second body having a lower end portion, a lower surface and an upper portion, a power supplying portion and a circuit portion and a second joint portion attachable and deattachable to said first joint portion of said first frame at one end portion thereof and wherein said second joint portion comprises an insertion end portion integrally formed at a lower end portion of said second body and insertable along said guide portion of said first frame for attaching and deattachinq;
a pair of electrodes each having two end portions, one end portion thereof being disposed to electrically contact said contacting portions and the other end portion thereof being disposed on said upper surface of said first frame;
an electrically conductive means for electrically connecting said power supplying portion with said electrodes formed on said lower surface of said second frame; and
an insertion member comprising a third body having two ends, located at said upper surface of said LCD window, a plurality of insertion holes corresponding to the plurality of said latching end portions of said first frame, and electrode grooves formed at both ends of said third body, and said pair of electrodes each having two end portions, wherein one end portion thereof being disposed to electrically contact with said contacting portions and the other end portion thereof being insertable and fixable into said electrode grooves.

2. A shading device for a welding helmet as claimed in claim 1, wherein said first frame further comprises:
an insertion hole formed at said upper surface of said first body in a lengthwise direction in order to separate said LCD module from said first body.

3. A shading device for a welding helmet as claimed in claim 1, wherein:
said power supplying portion comprises a solar cell module and a battery having a battery cassette.

4. A shading device for a welding helmet as claimed in claim 3, further comprising:
means for locking said battery cassette formed at said second body of said second frame for restricting a jointing status between said first and second frame and releasing the restriction thereof, said means for locking comprising a fourth body having a lower end portion and an upper portion having a window with an inside and a latching end portion formed at said lower end portion of said fourth body; a supporter attached to said upper portion of said second body and traversing said window at a right angle; a stopper located at said inside of said window and attached to said second body; a spring for inserting said supporter therein and interposed between said upper portion of said fourth body and said stopper; and an insertion through hole formed at said lower end portion of said second body in order to restrict said latching end portion or release the restriction of said latching end portions by the elasticity of said spring corresponding to the attachment or the deattachment of said battery cassette.

5. A shading device for a welding helmet as claimed in claim 1, wherein:
said electrically conductive means comprises openings located at a lower portion of said insertion end portion corresponding to said electrodes, a supporter mounted on an inside of each opening; and each spring comprising one end portion wound on said supporter and the other end portion thereof being disposed to electrically connect to said electrodes.

6. A shading device for a welding helmet comprising:
a first frame comprising a first body with an upper end portion and an upper surface having side portions, said first body having an LCD module having an LCD window with two opposite sides and an upper surface and a contacting portion formed at each of said opposite sides of said LCD window and a first joint portion formed at said upper end portion of said first body;
a second frame comprising a second body having a lower end portion, a lower surface and an upper portion, a power supplying portion and a circuit portion and a second joint portion attachable and deattachable to said first joint portion of said first frame at one end portion thereof, wherein said power supplying portion comprises a solar cell module and a battery having a battery cassette;
a pair of electrodes each having two end portions, one end portion thereof being disposed to electrically contact said contacting portions and the other end portion thereof being disposed on said upper surface of said first frame;

an electrically conductive means for electrically connecting said power supplying portion with said electrodes formed on said lower surface of said second frame; and means for locking said battery cassette formed at said second body of said second frame for restricting a jointing status between said first and second frame and releasing the restriction thereof, said means for locking comprising a fourth body having a lower end portion and an upper portion having a window with an inside and a latching end portion formed at said lower end portion of said fourth body; a supporter attached to said upper portion of said second body and traversing said window at a right angle; a stopper located at said inside of said window and attached to said second body; a spring for inserting said supporter therein and interposed between said upper portion of said fourth body and said stopper; and an insertion through hole formed at said lower end portion of said second body in order to restrict said latching end portion or release the restriction of said latching end portions by the elasticity of said spring corresponding to the attachment or the deattachment of said battery cassette.

7. A shading device for a welding helmet as claimed in claim 6, wherein:

said first joint portion comprises a guide portion formed adjacent to said upper surface of said first body and a plurality of latching end portions formed at one of said side portions of the upper surface of said first body, and wherein said second joint portion comprises an insertion end portion integrally formed at a lower end portion of said second body and insertable along said guide portion of said first frame for attaching and deattaching.

8. A shading device for a welding helmet as claimed in claim 7, wherein the shading device further comprises:

an insertion member comprising a third body having two ends, located at said upper surface of said LCD window, a plurality of insertion holes corresponding to the plurality of said latching end portions of said first frame, and electrode grooves formed at both ends of said third body, and said pair of electrodes each having two end portions, wherein one end portion thereof being disposed to electrically contact with said contacting portions and said other end portion thereof being insertable and fixable into said the electrode grooves.

9. A shading device for a welding helmet as claimed in claim 8, wherein the first frame further comprises:

an insertion hole formed at said upper surface of said first body in a lengthwise direction in order to separate said LCD module from said first body.

10. A shading device for a welding helmet as claimed in claim 6, wherein:

said electrically conductive means comprises openings located at a lower portion of said insertion end portion corresponding to said electrodes, a supporter mounted on an inside of each opening; and each spring comprising one end portion wound on said supporter and said other portion thereof being disposed to electrically connect to said electrodes.

* * * * *